US00PP31829P2

(12) United States Plant Patent
Podaras

(10) Patent No.: US PP31,829 P2
(45) Date of Patent: Jun. 2, 2020

(54) ***BUDDLEIA* PLANT NAMED 'PODARASNGA1'**

(50) Latin Name: ***Buddleia x hybrida* (*Buddleia davidii* x *B. crispa* x *B. alternifolia* x *B. lindleyana*)**
Varietal Denomination: PODARASNGA1

(71) Applicant: Early Morning LLC, Greendale, IN (US)

(72) Inventor: Peter Podaras, Tipp City, OH (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 16/501,304

(22) Filed: Mar. 20, 2019

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 5/02; A01H 5/00
See application file for complete search history.

*Primary Examiner* — Kent L Bell
(74) *Attorney, Agent, or Firm* — Barbara Campbell; Cochran Freund & Young LLC

(57) ABSTRACT

A new *Buddleia* plant particularly distinguished by prodigious and perpetually blooming, large flowers from the ground all the way to the top on wide panicles, individual flowers are significantly larger than other varieties known to the inventor, and blooms June to frost, is disclosed.

2 Drawing Sheets

Genus and species: *Buddleia* x *hybrida* (*Buddleia davidii* x *B. crispa* x *B. alternifolia* x *B. lindleyana*).
Variety denomination: 'PODARASNGA1'.

BACKGROUND OF THE NEW PLANT

The present invention relates to a new and distinct variety of *Buddleia* hereinafter referred to by the variety name 'PODARASNGA1'.

'PODARASNGA1' arose from a controlled cross in Jul. 15, 2014 in Davis, Calif. between an unnamed and unpatented *Buddleia davidii* x *B. crispa* x *B. alternifolia* x *B. lindleyana* female parent, and an unnamed and unpatented *Buddleia davidii* x *B. crispa* x *B. alternifolia* x *B. lindleyana* male parent. Seeds from the cross were sown in April 2015 and 'PODARASNGA1' was selected in August 2015 from the seedling population.

'PODARASNGA1' was first asexually propagated in August 2016 in Wasco, Calif. by softwood cuttings. 'PODARASNGA1' was found to reproduce true to type in successive generations of asexual propagation via softwood cuttings.

SUMMARY

The following are the most outstanding and distinguishing characteristics of this new variety when grown under normal horticultural practices in Wasco, Calif. and Tipp City, Ohio.

1. Prodigious and perpetually blooming shrub;
2. Large flowers from the ground all the way to the top on wide panicles;
3. Individual flowers are significantly larger than other varieties known to the inventor; and
4. Blooms June to frost.

DESCRIPTION OF THE PHOTOGRAPHS

This new butterfly bush plant is illustrated by the accompanying photographs which shows the plant's overall plant habit including form, fruit, and foliage. The photographs are of a 2-year-old plant taken in August 2018 and grown outdoors in Tipp City, Ohio. The colors shown are as true as can be reasonably obtained by conventional photographic procedures.

Figure 1:
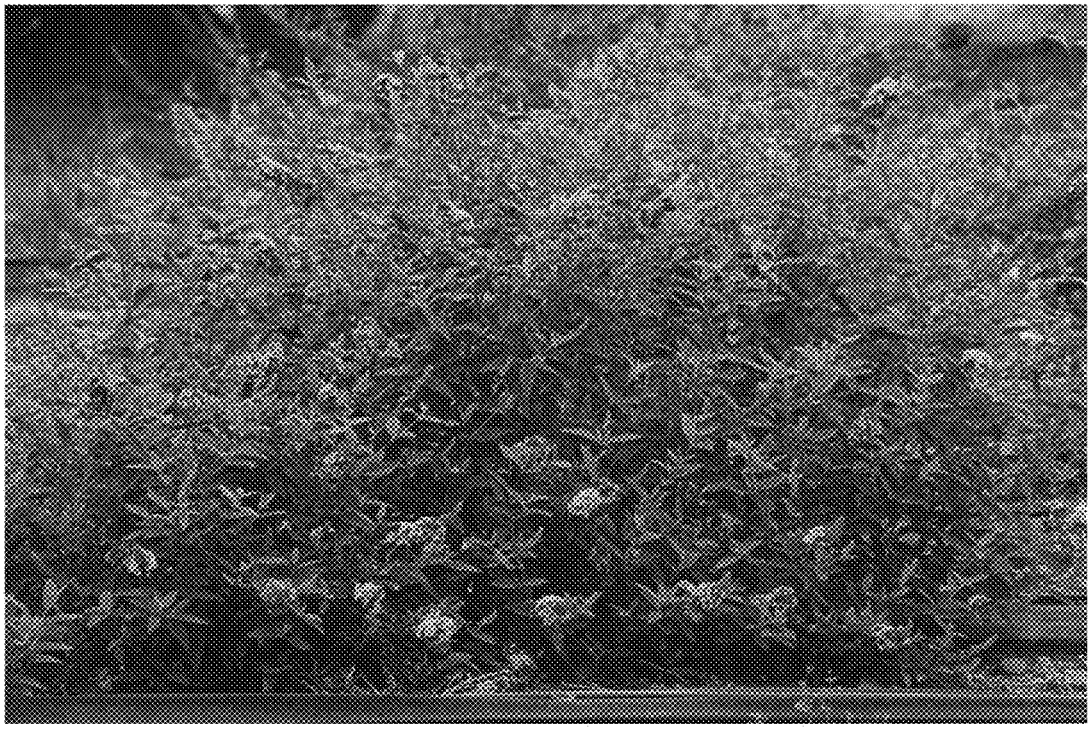
FIG. 1 shows the overall plant habit.
Figure 2:
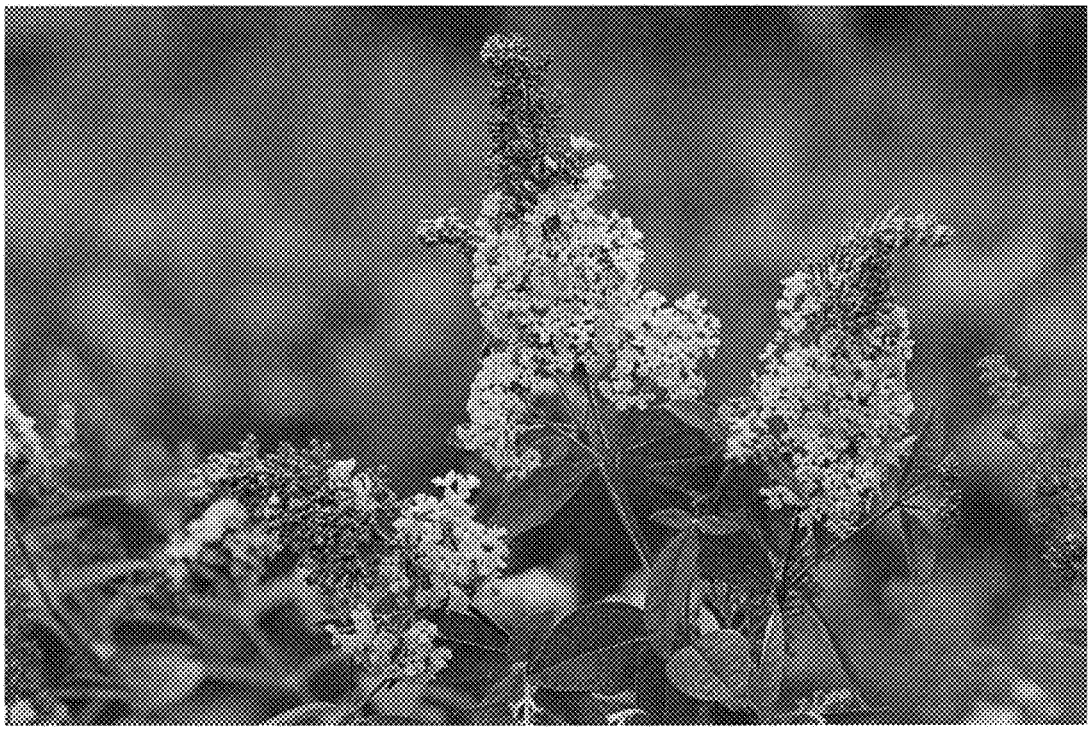
FIG. 2 shows a close-up the foliage, bud, and inflorescences of the plant.
Figure 3:
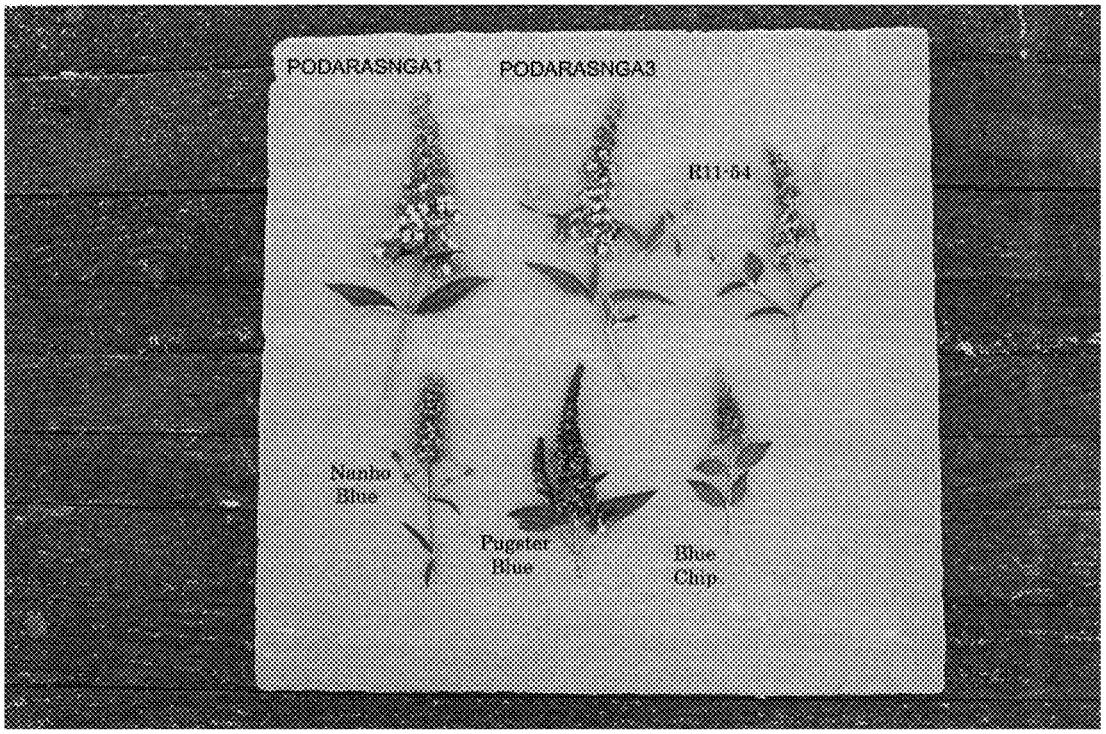

FIG. 3 shows individual inflorescence stems from several *Buddleia* lines. The top row shows from left to right, 'PODARASNGA1', 'PODARASNGA3' (U.S. Plant patent application Ser. No. 16/501,303), and 'R11-54', a proprietary line. The bottom row shows from left to right, the commercial lines, 'Nanho Blue', 'Pugster Blue', and 'Blue Chip'.

DESCRIPTION OF THE NEW VARIETY

The following detailed descriptions set forth the distinctive characteristics of 'PODARASNGA1'. Measurements were made in Tipp City, Ohio on a 2-year-old plant that has been cut back to the ground at the start of its second season of growth. Color references are to The R.H.S. Colour Chart of The Royal Horticultural Society of London (R.H.S.) 2007, Fifth Edition.

Classification:
- *Family*.—Scrophulariacace.
- *Botanical*.—*Buddleia* x *hybrida* (*Buddleia davidii* x *B. crispa* x *B. alternifolia* x *B. lindleyana*).
- *Designation*.—'PODARASNGA1'.

Plant:
- *Form*.—Shrub.
- *Habit*.—Dense spreading.
- *Height* (*measured from the top of the soil*).—168 cm.
- *Width* (*horizontal plant diameter*).—214 cm.
- *Time to produce a finished plant*.—2 to 3 months for a one-gallon finished plant.

*Outdoor plant performance.*—Excellent with good vigor and dense branching; continuous and plentiful blooms over the entire exterior of the plant; has new growth obscuring old spent blooms.

*Natural flowering season.*—June through frost.

*Time to initiate and develop roots.*—5 to 7 days using 1,500 to 3,000 ppm IBA.

*Root description and habit.*—Fibrous and dense.

*Propagation type.*—Softwood cuttings.

Lateral branches:

*Diameter (from midpoint).*—0.2 cm to 3.0 cm.

*Internode length.*—5.0 cm to 7.0 cm.

*Texture.*—Pubescent.

*Color.*—Upper surface: RHS 166A (Greyed-orange) (with indumentum rubbed off). Lower surface: RHS 146D (Yellow-green) (with indumentum rubbed off).

*Strength.*—Flexible.

*Anthocyanin.*—Absent.

Leaves:

*Leaf arrangement.*—Opposite.

*Length.*—7.0 cm to 7.5 cm.

*Width.*—1.5 cm to 3.0 cm.

*Shape.*—Simple lanceolate.

*Apex.*—Acute.

*Base.*—Acuminate.

*Margin.*—Subtle irregular serration; serrations are widely spaced; serration is absent on most of the basal half of the leaf and more frequent to the tip.

*Texture.*—Upper surface: Sessile stellate hairs mostly 4 to a cluster sometimes with a glandular body in the center; clusters of hairs dense and overlapping toward the veins. Lower surface: Very floccose in interveinal areas and sparse or absent on the veins.

*Color, immature.*—Upper surface: RHS 136A (Green). Lower surface: RHS 191C (Greyed-green).

*Color, mature.*—Upper surface: RHS 139A (Green). Lower surface: 194A (Greyed-green).

*Venation pattern.*—Reticulate.

*Venation color.*—Upper surface: RHS 136A (Green). Lower surface: RHS 191C (Greyed-green).

*Petiole.*—Length: 0.3 cm. Diameter: 0.15 cm. Texture: Floccose, especially on the lower side.

Inflorescence (panicle):

*Appearance.*—Naked and multiples of individual blooms arranged on a blunt and tipped conical structure that eventually becomes a panicle, which are roughly conical in shape.

*Height.*—11.0 cm to 15.0 cm.

*Width.*—5.0 cm to 7.0 cm.

*Bud.*—Shape: Conical. Height: 1.0 cm. Diameter: 0.5 cm. Color: RHS 194C (Greyed-green) or RHS 194B (Greyed-green).

*Flower.*—Type and habit: Single and salverform flowers arranged in compound terminal panicles; flowers face upright and outward. Fragrance: Sweetly fragrant. Lastingness of flowers on the plant: 5 to 7 days. Quantity of flowers per inflorescence (panicle): 200 to 275. Depth: 1.5 cm. Diameter: 0.9 cm.

*Petals.*—Arrangement: Four arranged in a single whorl with the petals fused into a narrow tube. Shape: Reniform. Apex: Obtuse. Base: Truncated and fused to the corolla tube; there is a distinctive notch and then a miniscule lobe at the point of fusion to the corolla tube on either side of the petal. Margin: Crenate. Texture: Upper surface: Smooth. Lower surface: Longitudinal wrinkles along the entire length. Length: 0.4 cm. Width: 0.5 cm at its widest point. Color, immature and mature: Upper surface: Outer edge is RHS 92A (Violet-blue) and RHS 162B (Greyed-yellow) towards the center. Lower surface: RHS 92A (Violet-blue).

*Corolla tube.*—Length: 1.1 cm. Width: 0.15 cm. Color: Inner surface: RHS 166C (Greyed-orange). Outer surface: RHS 172A (Greyed-orange). Texture: Inner surface: Pubescent; dense, single hairs. Outer surface: Stellate hairs, with 4 to a cluster.

*Calyx.*—Arrangement and quantity per flower: Four sepals arranged in a single whorl and fused at the base. Sepals: Shape: Reniform (for the one quarter top part of the sepal). Apex: Acute. Base: Fused into a tube (three-quarter lower part of the sepal). Margin: Undulate. Length: 0.3 cm. Width: 0.095 cm. Texture: Upper surface: Floccose, covered in clusters of sessile, stellate hairs. Lower surface: Smooth. Color: Upper surface: RHS N186C (Greyed-purple) at the very edge of the apex. Lower surface: RHS 191C (Greyed-green) blending with RHS N186C (Greyed-purple) on sides exposed to direct sunlight.

*Peduncle.*—Length: 4.5 cm. Diameter: 2.5 cm. Strength: Strong, slightly pliable, bends but does not snap. Color: RHS N199B (Grey-brown). Texture: Pubescent, covered with stellate hairs.

*Pedicel.*—Length: 0.1 cm. Diameter: 0.05 cm. Color: RHS 194B (Greyed-green). Texture: Pubescent.

Reproductive organs:

*Stamens.*—Quantity per flower: 4. Filament: Length: 0.8 cm. Color: RHS 157C (Green-white). Anther: Length: 0.2 cm. Color: RHS 159C (Orange-white). Pollen amount: Moderate. Pollen color: RHS 159C (Orange-white).

*Pistil.*—Quantity per flower: 1. Length: 0.12 cm. Stigma: Shape: Oblong with distinct bilateral symmetry; occasional minute apical protuberance from apex of differing sizes. Color: RHS 137B (Green). Style: Length: 0.15 cm. Color: RHS 145B (Yellow-green). Ovary: Shape: Ovoid. Length: 0.18 cm. Width: 0.1 cm. Color: RHS 141D (Green).

Seed: Can produce a moderate amount of seed if there are other varieties of *Buddleia* nearby.

Disease and insect resistance: Very disease resistant but susceptible to spider mites in the greenhouse.

COMPARISON WITH PARENTAL LINES AND COMMERCIAL LINE

When 'PODARASNGA1' is compared to the female *Buddleia* parent, an un-named and unpatented line, the female parent has a weeping habit with large flowers, while 'PODARASNGA1' has a dense spreading with large flowers.

When 'PODARASNGA1' is compared to the male *Buddleia* parent, an un-named and unpatented line, the male parent has larger individual flowers on very wide panicles when compared to 'PODARASNGA1'.

When 'PODARASNGA1' is compared to the commercial line 'Lavender Veil', also known as 'Hinebud1' (U.S. Plant Pat. No. 23,498), 'PODARASNGA1' has a dense and spreading habit and shorter panicles, 11 cm to 15 cm in height, while 'Lavender Veil' has a low growing and spreading habit and longer panicles than 'PODARASNGA1'.

I claim:

1. A new and distinct variety of *Buddleia* plant named 'PODARASNGA1' as illustrated and described herein.

* * * * *